United States Patent

Sato et al.

[11] Patent Number: 6,037,342
[45] Date of Patent: Mar. 14, 2000

[54] SEROTONIN 5-HT$_3$ RECEPTOR PARTIAL ACTIVATOR

[75] Inventors: Yasuo Sato; Megumi Yamada; Kazuko Kobayashi; Katsuyoshi Iwamatsu; Fukio Konno, all of Kanagawa; Koichi Shudo, Tokyo, all of Japan

[73] Assignees: Meiji Seika Kaisha, Ltd; Koichi Shudo, both of Tokyo, Japan

[21] Appl. No.: 08/852,747

[22] Filed: May 6, 1997

[30] Foreign Application Priority Data

May 9, 1996 [JP] Japan ............................. 8-115008
Apr. 11, 1997 [JP] Japan ............................. 9-093821

[51] Int. Cl.$^7$ .................. A61N 43/62; C07D 243/08; C07D 403/00
[52] U.S. Cl. .................. 514/218; 540/575; 540/603
[58] Field of Search .................. 540/575, 603; 514/218

[56] References Cited

U.S. PATENT DOCUMENTS 5,631,257  5/1997  Iwamatsu et al. .

FOREIGN PATENT DOCUMENTS 0 621 271 A1  4/1994  European Pat. Off. .
370874  9/1963  Switzerland .

OTHER PUBLICATIONS

*Chemical Abstracts*, vol. 80, No. 25, Jun. 24, 1974, abstract No. 146143x, p. 444.

*Journal of Medicinal Chemistry*, vol. 37, No. 9, Apr. 29, 1994, "Synthesis of 2–piperazinylbenzothiazole and 2–piperazinylbenzoxazole derivatives with 5–HT3 antagonist and 5–HT4 agonist properties," by Antonio Monge et al. pp. 1320–1325.

*Journal of Medicinal Chemistry*, vol. 11, No. 5, Aug. 26, 1968, "Synthesis of 1,4–disubstituted piperazines", by Matthew Verderame, p. 1091.

*Chimica Therapeutica*, vol. 6, No. 2, Mar., 1971, Paris, "Aryl–2 benzoxazoles a action anti–inflammatoire", pp. 126–130.

*Primary Examiner*—Johann Richter
*Assistant Examiner*—Joseph Murray
*Attorney, Agent, or Firm*—Sughrue, Mion, Zinn, Macpeak & Seas, PLLC

[57] ABSTRACT

This invention provides a serotonin 5-HT$_3$ receptor partial activator which has a serotonin 5-HT$_3$ receptor activating action, in addition to its serotonin 5-HT$_3$ receptor antagonism, and does not cause constipation as a side effect. Particularly, based on the finding that newly synthesized benzoxazole derivatives typified by the compounds of the following formula (2) have strong serotonin 5-HT$_3$ receptor antagonism and serotonin 5-HT$_3$ receptor activating action, this invention provides these benzoxazole derivatives as serotonin 5-HT$_3$ receptor partial activators.

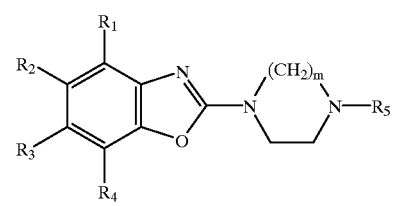

(2)

In the above formula, $R_1$ to $R_4$ may be the same or different from one another and each represents a hydrogen atom, a halogen atom, a substituted or unsubstituted lower alkyl group, a substituted or unsubstituted lower alkenyl group or a substituted or unsubstituted amino group, or two groups of $R_1$ and $R_2$ may be linked together to form a ring structure, namely benzene ring; $R_5$ represents a hydrogen atom, a substituted or unsubstituted lower alkyl group or a substituted or unsubstituted lower alkenyl group; and m is an integer of 1 to 4.

4 Claims, No Drawings

SEROTONIN 5-HT₃ RECEPTOR PARTIAL ACTIVATOR

FIELD OF THE INVENTION

This invention relates to novel and known benzoxazole derivatives, more particularly to a serotonin 5-HT₃ receptor antagonist or a serotonin 5-HT₃ receptor partial activator, which has been developed on the basis of the effective and selective action of said derivatives upon serotonin 5-HT₃ receptors that are distributed in smooth muscles such as of digestive organs and the like and in central nervous system, intestinal nervous system and the like.

BACKGROUND OF THE INVENTION

It has been revealed that serotonin 5-HT₃ receptor antagonists can inhibit nausea and emesis as side effects caused by the use of cisplatin and the like carcinostatic agents and by radiation treatments, and several compounds thereof are now used in the clinical field. In addition to this, development on their use as digestive organ function controlling drugs has recently been examined.

The inventors of the present invention have already found that certain benzoxazole derivatives are possessed of serotonin 5-HT₃ receptor antagonism (JP-A-6-345744; the term "JP-A" as used herein means an "unexamined published Japanese patent application").

When a compound having only serotonin 5-HT₃ receptor antagonism is administered as a digestive organ function controlling drug, it can inhibit diarrhea but poses a problem of frequently causing constipation as a side effect.

SUMMARY OF THE INVENTION

In view of the above, it therefore becomes an object of the present invention to provide a serotonin 5-HT₃ receptor partial activator which is possessed of not only serotonin 5-HT₃ receptor antagonism but also serotonin 5-HT₃ receptor activating action and is useful in getting rid of constipation side effect.

Using an evaluation test system in which serotonin 5-HT₃ receptor antagonizing and activating actions are judged by a guinea pig excised ileum contraction action which can be used as an index of the serotonin 5-HT₃ receptor activating action upon digestive organs, the inventors of the present invention have found that certain compounds among the benzoxazole derivatives disclosed in JP-A-345744 are possessed of serotonin 5-HT₃ receptor partial activity. As a result of subsequent synthesis and evaluation studies, it was found that certain novel or known benzoxazole derivatives are possessed of not only serotonin 5-HT₃ receptor antagonism but also serotonin 5-HT₃ receptor activating action and are useful as strong serotonin 5-HT₃ receptor partial activators. The present invention has been accomplished on the basis of these findings.

Accordingly, the gist of the present invention resides in the compounds of the following formulae (1) to

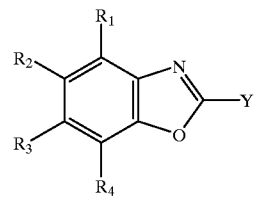

(1)

wherein $R_1$ to $R_4$ may be the same or different from one another and each represents a hydrogen atom, a halogen atom, a substituted or unsubstituted lower alkyl group, a substituted or unsubstituted lower alkenyl group or a substituted or unsubstituted amino group, or optional two groups of $R_1$ to $R_4$ may be linked together to form a ring structure which is a 5- or 6-membered ring composed of carbon atoms alone or carbon atoms and 1 to 2 hetero atoms, selected from a cyclohexane ring, a benzene ring, a pyridine ring, a piperidine ring and a pyrrolidine ring; and Y represents a saturated or unsaturated, substituted or unsubstituted 4- to 8-membered hetero ring containing 1 to 3 nitrogen atoms as the ring constituting atoms and carbon atoms as the remaining atoms, which is selected from the group consisting of an azetidine ring, a pyrrolidine ring, a piperidine ring, a pyridine ring, an imidazole ring, a pyrazinyl ring, a pyridazinyl ring, a triazole ring, a homopiperidine ring, a 1,4-diazacyclooctanyl ring and a 1,5-diazacyclooctanyl ring;

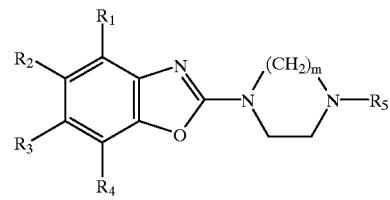

(2)

wherein $R_1$ to $R_4$ may be the same or different from one another and each represents a hydrogen atom, a halogen atom, a substituted or unsubstituted lower alkyl group, a substituted or unsubstituted lower alkenyl group or a substituted or unsubstituted amino group, or two groups of $R_1$ and $R_2$ may be linked together to form a ring structure, namely a benzene ring, with the proviso that compounds in which all of $R_1$ to $R_4$ are hydrogen atoms are excluded; $R_5$ represents a hydrogen atom, a substituted or unsubstituted lower alkyl group or a substituted or unsubstituted lower alkenyl group; and m is an integer of 1 to 4; and

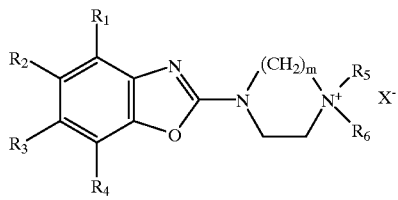

(3)

wherein $R_1$ to $R_4$ may be the same or different from one another and each represents a hydrogen atom, a halogen atom, a substituted or unsubstituted lower alkyl group, a substituted or unsubstituted lower alkenyl group or a substituted or unsubstituted amino group, or two groups of $R_1$ and $R_2$ may be linked together to form a ring structure, namely a benzene ring, with the proviso that compounds in which all of $R_1$ to $R_4$ are hydrogen atoms are excluded; $R_5$ and $R_6$ may be the same or different from each other and each represents a substituted or unsubstituted lower alkyl group or a substituted or unsubstituted lower alkenyl group; m is an integer of 1 to 4; and $X^-$ represents a halogen ion.

Further, the second aspect of the present invention resides in a serotonin 5-HT$_3$ receptor partial activator containing, as an active ingredient, the compounds of any one of the formulae (1) to (3) or a compound represented by the formula (4) shown hereinafter, for example, for use in the treatment and prevention of functional disorders of digestive organs and diarrhea.

Other objects and advantages of the present invention will be made apparent as the description progresses.

DETAILED DESCRIPTION OF THE INVENTION

In the aforementioned formula (1), examples of the ring structure represented by Y include an azetidine ring, a pyrrolidine ring, a piperidine ring, a pyridine ring, an imidazole ring, a pyrazinyl ring, a pyridazinyl ring, a triazole ring, a homopiperidine ring, a 1,4-diazacyclooctanyl ring and a 1,5-diazacyclooctanyl ring. Preferably, Y is 4-pyridinyl group, 4-piperidinyl group, 4-homopiperidinyl group, 3-pyrrolidinyl group, 1-(1,4-diazacyclooctanyl) group or 1-(1,5-diazacyclooctanyl) group.

The substituent of Y is a group which is linked to a nitrogen atom of Y and selected from the group consisting of a straight or branched $C_1$–$C_4$ alkyl group and a straight or branched $C_2$–$C_4$ alkenyl group, and at least one hydrogen atom of the alkyl or alkenyl group may be substituted with a substituent group which may be selected from the group consisting of a hydroxyl group, a halogen atoms, a carbamoyl group, an amino group and a cyano group.

Particularly preferred compounds of the formula (2) are those in which $R_1$ to $R_4$ may be the same or different from one another and each represents a hydrogen atom, a halogen atom or a substituted or unsubstituted lower alkyl group, or two groups of $R_1$ and $R_2$ may be linked together to form a benzene ring; $R_5$ is a substituted or unsubstituted lower alkyl group; and m is an integer of 2 or 3, with the proviso that compounds in which all of $R_1$ to $R_4$ are hydrogen atoms are excluded because such compounds are disclosed in JP-A-6-345744.

Definition

According to this specification, the alkyl or alkenyl as a group or a part of a group may be either straight chain or branched chain. Also in this specification, the term halogen atom means fluorine, chlorine, bromine or iodine atom.

Compounds of Formulae (1) to (3)

In the formulae (1) to (3), the lower alkyl group represented by any one of $R_1$ to $R_6$ is a $C_1$–$C_4$ alkyl group, and at least one hydrogen atom of the alkyl group may be substituted with a substituent group which may be selected from the group consisting of a halogen atom, a hydroxyl group, a carbamoyl group, an amino group and a cyano group.

The lower alkenyl group represented by any one of $R_1$ to $R_4$ is a $C_2$–$C_4$ alkenyl group, and at least one hydrogen atom of the alkenyl group may be substituted with a substituent group which may be selected from the group consisting of a hydroxyl group, a halogen atoms, a carbamoyl group, an amino group and a cyano group.

Examples of the substituent group of the amino group represented by any one of $R_1$ to $R_4$ include those which are selected from the group consisting of a straight or branched $C_1$–$C_4$ alkyl group, a straight or branched $C_1$–$C_4$ alkylcarbonyl group, a straight or branched $C_2$–$C_4$ alkenyl group and a benzylidene group which may have a phenyl group.

Use and Pharmaceutical Composition of the Compounds of Formulae (1) to (3) and a Compound of Formula (4)

According to the present invention, the compounds of formulae (1) to (3) and a compound represented by formula (4):

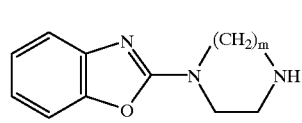

(wherein m is an integer of 1 to 4) are possessed of serotonin 5-HT$_3$ receptor antagonism and serotonin 5-HT$_3$ receptor activating action. In consequence, they are useful as drugs for the treatment and prevention of diseases in which serotonin 5-HT$_3$ is concerned. Examples of the serotonin 5-HT$_3$-concerned diseases include emesis caused by the use of cisplatin and the like carcinostatic agents or by radiation treatments, as well as difficulty of gastrointestinal moving, irritable colon syndrome, headache, neuralgia, anxiety, depression, psychosis and the like.

In addition to the serotonin 5-HT$_3$ receptor antagonism, the compounds of formulae (1) to (4) of the present invention also show serotonin 5-HT$_3$ receptor partial activation action having serotonin 5-HT$_3$ receptor activating action, so that they are particularly useful in the treatment and prevention of difficulty of gastrointestinal moving and irritable colon syndrome as a digestive organ function controlling drug which can inhibit diarrhea without causing constipation as a side effect.

The compounds of formulae (1) to (4) of the present invention can be used in the form of free bases or as pharmaceutically acceptable salts thereof. For example, the compounds of formulae (1), (2) and (4) can be administered in the form of an appropriate acid addition salt or quaternary ammonium salt. As such salts, pharmaceutically acceptable non-toxic salts can be exemplified. Preferred examples thereof include salts with hydrohalogenic acids such as hydrofluoric acid, hydrochloric acid, hydrobromic acid, hydroiodic acid and the like, inorganic acid salts such as sulfate, nitrate, phosphate, perchlorate, carbonate and the like, salts with carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, malic acid and the like, salts with acidic amino acids such as aspartic acid, glutamic acid and the like and salts with organic acids such as methanesulfonic acid, p-toluenesulfonic acid and the like. In addition, the compound of formula (3) is administered as a salt of a halogen anion such as chlorine, bromine, iodine or the like represented by $X^-$ of the formula (3). Such salts of the compounds of formulae (1) to (4) show the same level of activities of the corresponding free bases. In consequence, the compounds represented by the general formulae (1) to (4), acid addition salts thereof and quaternary ammonium salts thereof are all included in the present invention.

Illustrative examples of more particularly preferred compounds of the present invention include, in the case of formula (1), 2-(4-pyridyl)benzoxazole,
2-(4-piperidyl)benzoxazole,
2-(4-piperidyl)-5-methylbenzoxazole,
5-chloro-2-(1-piperidyl)benzoxazole and
5,7-dimethyl-2-(1,4-diazacyclooctanyl)benzoxazole,
in the case of formula (2),
5-chloro-2-(4-methyl-1-piperazinyl)benzoxazole,
5,7-dimethyl-2-(4-methyl-1-piperazinyl)benzoxazole,
6-amino-5-chloro-2-(4-methyl-1-piperazinyl)benzoxazole,
6-methylamino-5-chloro-2-(4-methyl-1-piperazinyl) benzoxazole,
6-benzylideneamino-5-chloro-2-(4-methyl-1-piperazinyl) benzoxazole,
5-methyl-2-(1-piperazinyl)benzoxazole,
6-amino-5-chloro-2-(1-piperazinyl)benzoxazole,
6-dimethylamino-5-chloro-2-(4-methyl-1-piperazinyl) benzoxazole,
5,7-dimethyl-2-(1-piperazinyl)benzoxazole,
2-(4-methyl-1-piperazinyl)-5-methylbenzoxazole,
2-(4-methyl-1-piperazinyl)-6-methylbenzoxazole,
2-(4-methyl-1-piperazinyl)-7-methylbenzoxazole,
2-(4-methyl-1-piperazinyl)-5,7-dichlorobenzoxazole,
2-(4-methyl-1-piperazinyl)naphtho[1,2-d]oxazole,
2-(4-methyl-1-piperazinyl)-5-aminobenzoxazole,
2-(4-methyl-1-piperazinyl)-6-aminobenzoxazole,
2-(4-methyl-1-piperazinyl)-5-trifluoromethylbenzoxazole,
5-chloro-7-methyl-2-(4-methyl-1-piperazinyl)benzoxazole,
5-chloro-6,7-dimethyl-2-(4-methyl-1-piperazinyl) benzoxazole,
5,7-dichloro-6-methyl-2-(4-methyl-1-piperazinyl) benzoxazole,
5-methyl-2-(4-methyl-1-homopiperazinyl)benzoxazole,
5,7-dimethyl-2-(4-methyl-1-homopiperazinyl)benzoxazole,
5-chloro-7-methyl-2-(4-methyl-1-homopiperazinyl) benzoxazole,
5-chloro-7-ethyl-2-(4-methyl-1-homopiperazinyl) benzoxazole,
5-chloro-6-methyl-2-(4-methyl-1-homopiperazinyl) benzoxazole,
2-(4-methyl-1-homopiperazinyl)naphtho[1,2-d]oxazole,
5-chloro-2-(4-methyl-1-homopiperazinyl)benzoxazole,
5-chloro-6-amino-2-(4-methyl-1-homopiperazinyl) benzoxazole,
5,7-dimethyl-2-(1,4-diazacyclooctanyl)benzoxazole and
5,7-dimethyl-2-(4-methyl-1,4-diazacyclooctanyl) benzoxazole,
in the case of formula (3),
1-allyl-1-methyl-4-(5-chlorobenzoxazol-2-yl)piperazinium iodide,
1-allyl-1-methyl-4-(5,7-dimethylbenzoxazol-2-yl) piperazinium iodide,
1-allyl-1-methyl-4-(6-amino-5-chlorobenzoxazol-2-yl) piperazinium bromide,
1-allyl-1-methyl-4-(5-methylbenzoxazol-2-yl)piperazinium bromide,
1-allyl-1-methyl-4-(5-trifluoromethylbenzoxazol-2-yl) piperazinium bromide,
1-allyl-1-methyl-4-(6-methylbenzoxazol-2-yl)piperazinium bromide,
1-allyl-1-methyl-4-(7-methylbenzoxazol-2-yl)piperazinium bromide,
1-allyl-1-methyl-4-(5,7-dichlorobenzoxazol-2-yl) piperazinium bromide and
1-allyl-1-methyl-4-(naphtho[1,2-d]benzoxazol-2-yl) piperazinium bromide, and
in the case of formula (4),
2-(1-piperazinyl)benzoxazole.

A pharmaceutical composition which comprises the compound of the present invention as its active ingredient can be administered to human and animals other than human through the route of administration of either oral or parenteral (for example, intravenous injection, intramuscular injection, subcutaneous administration, percutaneous administration and the like).

In consequence, the pharmaceutical composition which contains the compound of the present invention as its active ingredient is made into appropriate dosage forms depending on the route of administration. Illustrative examples of oral dosage forms include tablets, capsules, powders, granules, syrups and the like, and those of parenteral dosage forms include intravenous, intramuscular and the like injections, rectal administration preparations, oleaginous suppositories, aqueous suppositories and the like. These various types of preparations can be produced in the usual way making use of generally used fillers, disintegrators, binders, lubricants, coloring agents and the like.

Illustrative examples of non-toxic fillers which can be used include lactose, glucose, corn starch, sorbitol, crystalline cellulose and the like, those of disintegrators include starch, sodium alginate, gelatin, calcium carbonate, calcium citrate, dextrin and the like, those of binders include dimethyl cellulose, polyvinyl alcohol, polyvinyl ether, methyl cellulose, ethyl cellulose, acacia, hydroxypropyl cellulose, polyvinyl pyrrolidone and the like and those of lubricants include talc, magnesium stearate, polyethylene glycol, hardened oil and the like.

In the case of injections, a buffer, a pH adjusting agent, an stabilizing agent and the like may be added as occasion demands.

Amount of the drug of the present invention to be contained in the pharmaceutical composition varies depending on the dosage form, but is generally from 0.05 to 50% by weight, preferably from 0.1 to 20% by weight, based on the total composition.

Its dose is optionally decided in each case by taking age, body weight, sex, difference in diseases, degree of symptoms and the like of each patient into consideration, but is generally from 0.5 to 1,000 mg, preferably from 1 to 300 mg, per adult per day when used as a digestive organ function controlling drug, and the daily dose may be administered once a day or by dividing it into several doses per day.

Production of the compound of formula (1)

The compound of formula (1) of the present invention can be produced by various methods, but it may be produced preferably by the following two typical methods in the case of a compound in which a carbon atom of Y is linked to the benzoxazole ring.

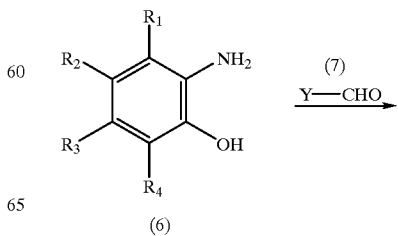

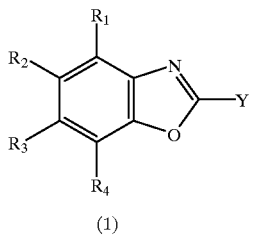

(1)

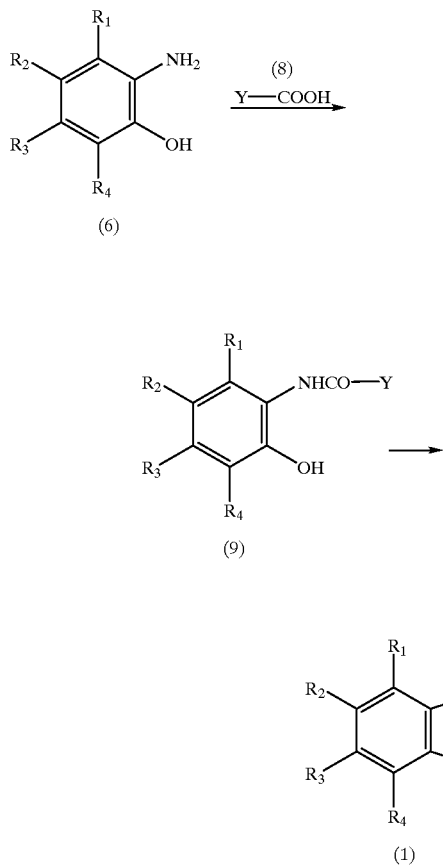

A compound represented by the formula (6) (in the formula, $R_1$, $R_2$, $R_3$ and $R_4$ are as defined in the formula (1)) is allowed to react with 1 to 10 equivalents of an aldehyde represented by the formula (7) (in the formula, Y is as defined in the formula (1)), thereby obtaining, among the intended compounds of formula (1) (in the formula, $R_1$, $R_2$, $R_3$, $R_4$ and Y are as defined in the foregoing), a compound in which a carbon atom of Y is linked to the benzoxazole ring.

Alternatively, a compound represented by the formula (6) (in the formula, $R_1$, $R_2$, $R_3$ and $R_4$ are as defined in the formula (1)) is allowed to react with 1 to 10 equivalents of a carboxylic acid represented by the formula (8) (in the formula, Y is as defined in the formula (1)) to obtain the compound of formula (9) (in the formula, $R_1$, $R_2$, $R_3$, $R_4$ and Y are as defined in the formula (1)) which is then subjected to cyclization, thereby obtaining, among the intended compounds of formula (1) (in the formula, $R_1$, $R_2$, $R_3$, $R_4$ and Y are as defined in the foregoing), a compound in which a carbon atom of Y is linked to the benzoxazole ring.

In the case of a compound in which a nitrogen atom of Y is linked to the benzoxazole ring, it can be produced preferably by the following method.

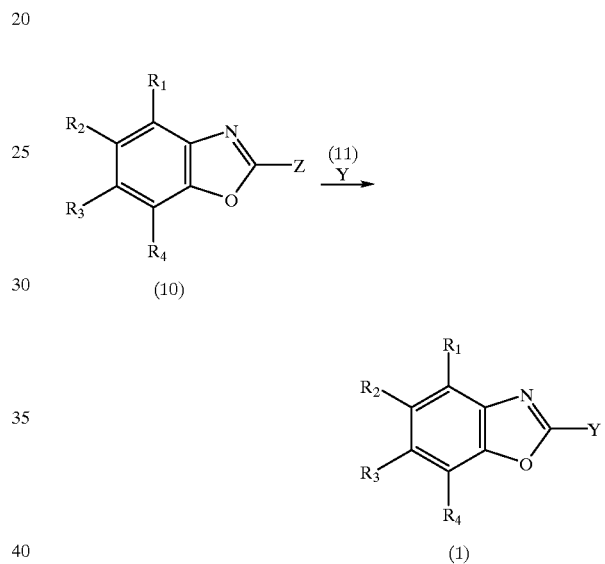

A compound represented by the formula (10) (in the formula, $R_1$, $R_2$, $R_3$ and $R_4$ are as defined in the formula (1) and Z represents a halogen atom or a thiol group) is allowed to react with 1 to 50 equivalents of a compound of nitrogen-containing ring structure represented by the formula (11) (in the formula, Y is as defined in the formula (1)), thereby obtaining, among the intended compounds of formula (1) (in the formula, $R_1$, $R_2$, $R_3$, $R_4$ and Y are as defined in the foregoing), a compound in which a nitrogen atom of Y is linked to the benzoxazole ring.

Production of the compounds of formulae (2) and (4)

The compound represented by the formula (2) or (4) can be produced preferably by the following two typical methods.

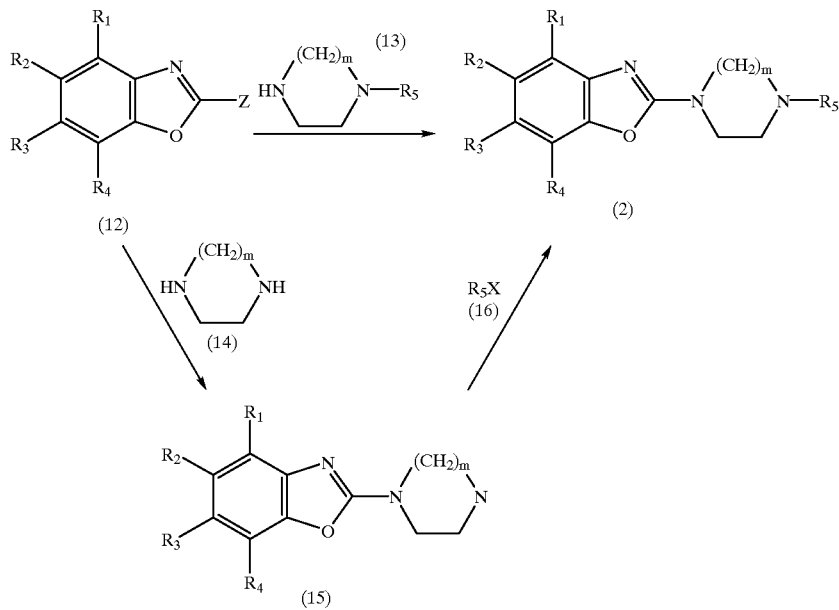

A compound represented by the formula (12) (in the formula, $R_1$, $R_2$, $R_3$ and $R_4$ are as defined in the formula (2) and Z is a halogen atom or a thiol group) is allowed to react with 1 to 50 equivalents of an N-substituted alicyclic diamine represented by the formula (13) (in the formula, $R_5$ is a substituted or unsubstituted lower alkyl group or a substituted or unsubstituted lower alkenyl group and m is as defined in the formula (2)), thereby obtaining the intended compound of formula (2) (in the formula, $R_1$, $R_2$, $R_3$, $R_4$ and m are as defined in the foregoing and $R_5$ is a substituted or unsubstituted lower alkyl group or a substituted or unsubstituted lower alkenyl group).

Alternatively, a compound represented by the formula (12) (in the formula, $R_1$, $R_2$, $R_3$ and $R_4$ are all hydrogen atoms or as defined in the formula (2) and Z is a halogen atom or a thiol group) is allowed to react with an alicyclic diamine represented by the formula (14) (in the formula, m is as defined in the formula (2)) to convert into the compound of formula (15) (in the formula, $R_1$, $R_2$, $R_3$ and $R_4$ are all hydrogen atoms or as defined in the formula (2) and m is as defined in the formula (2)) which is a compound of the formula (2) in which $R_5$ is hydrogen atom or a compound of the formula (4), subsequently allowing the resulting compound to react with 1 to 5 equivalents of a compound represented by the formula (16) (in the formula, $R_5$ is a substituted or unsubstituted lower alkyl group or a substituted or unsubstituted lower alkenyl group and X is a halogen atom), thereby obtaining the intended compound of formula (2) (in the formula, $R_1$, $R_2$, $R_3$, $R_4$ and m are as defined in the formula (2) and $R_5$ is a substituted or unsubstituted lower alkyl group or a substituted or unsubstituted lower alkenyl group).

Production of the compound of formula (3)

The compound represented by the formula (3) can be produced preferably by the following method.

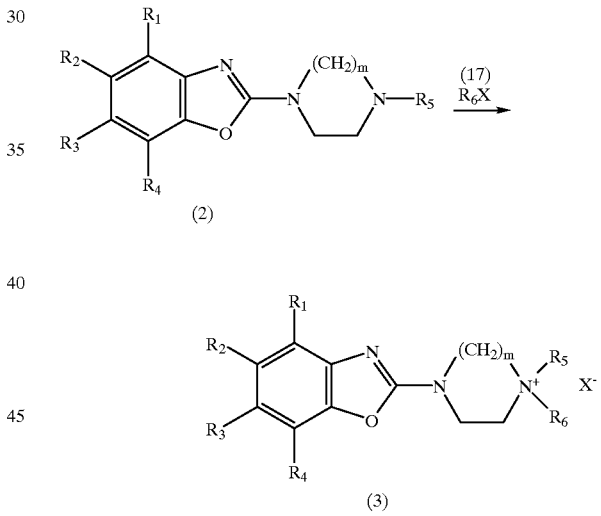

That is, a compound represented by the formula (2) (in the formula, $R_1$, $R_2$, $R_3$, $R_4$ and m are as defined in the formula (2) and $R_5$ is a substituted or unsubstituted lower alkyl group or a substituted or unsubstituted lower alkenyl group) is allowed to react with 1 to 10 equivalents of a compound represented by the formula (17) (in the formula, $R_6$ is as defined in the formula (3) and X is a halogen atom), thereby obtaining the intended compound of formula (3) (in the formula, $R_1$, $R_2$, $R_3$, $R_4$, $R_5$, $R_6$ and m are as defined in the formula (3) and $X^-$ is a halogen ion).

The reaction of compound (6) with compound (7) is quickly completed when they are allowed to react with each other in an organic acid such as acetic acid, trifluoroacetic acid or the like at 0 to 150° C. for 1 to 12 hours.

The compound (9) can be obtained easily when the reaction of compound (6) with compound (8) is carried out in a solvent such as DMF or the like at 0 to 150° C. for 1 to 12 hours in the presence of a chlorination agent such as thionyl chloride or the like or a condensing agent such as DCC or the like. Also, cyclization of the compound (9) is quickly completed within 1 to 24 hours when it is allowed to undergo the reaction at 50 to 150° C. in DMF or the like solvent in the presence of PPTS or the like acid catalyst or when it is heated at 50 to 200° C. together with polyphosphoric acid without solvent.

The reaction of compound (10) with compound (11) is quickly completed when they are allowed to react with each other without solvent or in DMF or the like solvent in the presence of triethylamine or the like alkylamine base at 0 to 150° C. for 1 to 12 hours.

The reaction of compound (12) with compound (13) or (14) is quickly completed when they are allowed to react with each other without solvent or in DMF or the like solvent in the presence of triethylamine or the like alkylamine base at 0 to 150° C. for 1 to 12 hours.

Formation of the compound (2) or (3) by the reaction of compound (15) with compound (16) or the reaction of compound (2) with compound (17) can be effected easily when they are allowed to react with each other in DMF or the like solvent at 0 to 150° C. for 1 to 12 hours.

The following reference examples, inventive examples and test examples are provided to further illustrate the present invention. It is to be understood, however, that the examples are for purpose of illustration only and are not intended as a definition of the limits of the invention, and therefore that various variations and modifications can be made within the scope of the invention as a matter of course. The NMR data in the examples are $\delta$ values based on TMS internal standard when measured using 400 MHz NMR.

REFERENCE EXAMPLE 1
5-Chloro-2-mercaptobenzoxazole

A 2 g portion of 2-amino-4-chlorophenol was dissolved in 150 ml of ethanol, and the solution was mixed with 80 ml of carbon disulfide and 937 mg of potassium hydroxide and heated under reflux for 8 hours. The solvent was evaporated under a reduced pressure, and the residual oily mixture was mixed with 50 ml of 1 N hydrochloric acid aqueous solution and extracted with ethyl acetate. The organic layer was washed with saturated brine and dried with magnesium sulfate and then the solvent was evaporated under a reduced pressure. By recrystallizing the thus obtained mixture from ethyl acetate, the title compound (1.3 g) in light yellow color was obtained.

$^1$H-NMR (CD$_3$OD) $\delta$ values: 6.97 (1 H, dd), 7.14 (1 H, d), 7.17 (1 H, d); MS (EI): m/z 185 (M$^+$)

INVENTIVE EXAMPLE 1
5-Chloro-2-(4-methyl-1-piperazinyl)benzoxazole

A 300 mg portion of 5-chloro-2-mercaptobenzoxazole was suspended in 50 ml of anhydrous benzene, and the suspension was mixed with 404 mg of phosphorus pentachloride and heated under reflux for 3 hours. The reaction solution was cooled in an ice bath and, with stirring, 1.6 g of 1-methylpiperazine was added thereto. After 30 minutes of stirring, the ice bath was removed to carry out 12 hours of stirring at room temperature, and then the reaction solution was mixed with saturated sodium bicarbonate aqueous solution and extracted with ethyl acetate. The organic layer was washed with saturated brine and dried with magnesium sulfate and then the solvent was evaporated under a reduced pressure. Thereafter, the thus obtained mixture was purified by a silica gel column chromatography (ethyl acetate:methanol=20:1) to obtain the title compound (121 mg) in light yellow color.

$^1$H-NMR (CD$_3$OD) $\delta$ values: 2.35 (3 H, s), 2.60 (4 H, t), 3.70 (4 H, t), 7.02 (1 H, dd), 7.25 (1 H, d), 7.28 (1 H, d) MS (EI): m/z 251 (M$^+$)

INVENTIVE EXAMPLE 2
1-Allyl-1-methyl-4-(5-chlorobenzoxazol-2-yl) piperazinium iodide A 30 mg portion of 5-chloro-2-(4-methyl-1-piperazinyl) benzoxazole was dissolved in 5 ml of DMF, and the solution which was stirred at room temperature was mixed with 100 mg of allyl iodide and then stirred for 12 hours. The solvent was evaporated under a reduced pressure, and the thus obtained mixture was purified by an LH-20 gel chromatography (chloroform:methanol=1:1) to obtain the title compound (36 mg) in light yellow color.

$^1$H-NMR (CD$_3$OD) $\delta$ values: 2.35 (3 H, s), 2.60 (4 H, t), 3.70 (4 H, t), 7.02 (1 H, dd), 7.25 (1 H, d), 7.28 (1 H, d) MS (FAB): m/z 292 (M$^+$)

INVENTIVE EXAMPLE 3
5,7-Dimethyl-2-(4-methyl-1-piperazinyl) benzoxazole

Using 5,7-dimethyl-2-mercaptobenzoxazole, the title compound was obtained in the same manner as described in Inventive Example 1.

$^1$H-NMR (DCl) $\delta$ values: 2.39 (6 H, s), 3.03 (3 H, s), 3.30 (2 H, t), 3.64 (2 H, t), 3.75 (2 H, d), 4.41 (2 H, d), 6.83 (1 H, s), 7.00 (1 H, s); MS (EI): m/z 245 (M$^+$)

INVENTIVE EXAMPLE 4
1-Allyl-1-methyl-4-(5,7-dimethylbenzoxazol-2-yl) piperazinium iodide Using 5,7-dimethyl-2-(4-methyl-1-piperazinyl) benzoxazole, the procedure of Inventive Example 2 was repeated to obtain the title compound. $^1$H-NMR (CD$_3$OD) $\delta$ values: 2.24 (3 H, s), 2.29 (3 H, s), 3.13 (3 H, s), 3.50–3.70 (4 H, m), 3.85–3.95 (2 H, m), 4.03–4.13 (2 H, m), 4.12 (2 H, d), 5.65–5.75 (2 H, m), 6.00–6.15 (1 H, m), 6.68 (1 H, s), 6.89 (1 H, s) MS (FAB): m/z 286 (M$^+$)

INVENTIVE EXAMPLE 5
6-Amino-5-chloro-2-(4-methyl-1-piperazinyl)benzoxazole a) Using 5-chloro-6-nitro-2-mercaptobenzoxazole, the procedure of Inventive Example 1 was repeated to obtain 5-chloro-6-nitro-2-(4-methyl-1-piperazinyl)benzoxazole.

$^1$H-NMR (CD$_3$OD) $\delta$ values: 2.52 (3 H, s), 2.77 (4 H, t), 3.92 (4 H, t), 7.50 (1 H, s), 8.15 (1 H, s); MS (EI): m/z 296 (M$^+$)

b) A 50 mg portion of 5-chloro-6-nitro-2-(4-methyl-1-piperazinyl)benzoxazole obtained in the above step (a) was dissolved in 10 ml of methanol, and the solution was mixed with 3 ml of 1 N hydrochloric acid aqueous solution and 10 mg of Pd/C catalyst and then, after replacing the atmosphere in the reaction vessel by hydrogen gas, stirred at room temperature for 3 hours. The catalyst was removed by filtration and the solvent was concentrated under a reduced pressure. The residual oily matter was mixed with saturated sodium bicarbonate aqueous solution and extracted with ethyl acetate. The organic layer was washed with saturated brine and dried with magnesium sulfate, and then the solvent was evaporated under a reduced pressure. Thereafter, the thus obtained mixture was purified by a silica gel column chromatography (chloroform:methanol=20:1) to obtain the title compound (38 mg) in light yellow color.

$^1$H-NMR (CD$_3$OD) $\delta$ values: 2.30 (3 H, s), 2.54 (4 H, t), 3.59 (4 H, t), 6.82 (1 H, s), 7.09 (1 H, s); MS (EI): m/z 266 (M$^+$)

INVENTIVE EXAMPLE 6
6-Methylamino-5-chloro-2-(4-methyl-1-piperazinyl) benzoxazole A 50 mg portion of 6-amino-5-chloro-2-(4-methyl-1-piperazinyl)benzoxazole was dissolved in 5 ml of formic acid, and the solution was mixed with 3 ml of formaldehyde and stirred at room temperature for 3 hours. The solvent was concentrated under a reduced pressure, and the resulting oily matter was mixed with saturated sodium bicarbonate aqueous solution and extracted with ethyl acetate. The organic layer was washed with saturated brine and dried with magnesium sulfate, and then the solvent was evaporated under a reduced pressure. Thereafter, the thus obtained mixture was purified by a silica gel column chromatography (chloroform:methanol=20:1) to obtain the title compound (28 mg) in light yellow color.

$^1$H-NMR (CD$_3$OD) δ values: 2.32 (3 H, s), 2.55 (4 H, t), 2.70 (3 H, s), 3.6–3.7 (4 H, m), 6.85 (1 H, s), 7.21 (1 H, s) MS (EI): m/z 280 (M$^+$)

INVENTIVE EXAMPLE 7
1-Allyl-1-methyl-4-(6-amino-5-chlorobenzoxazol-2-yl)piperazinium bromide A 50 mg portion of 6-amino-5-chloro-2-(4-methyl-1-piperazinyl)benzoxazole was dissolved in 5 ml of DMF, and the solution, while stirring at room temperature, was mixed with 135 mg of allyl bromide and stirred for additional 2 hours. Thereafter, the solvent was evaporated under a reduced pressure and the thus obtained mixture was purified by an LH-20 gel column chromatography (chloroform:methanol=1:1) to obtain the title compound (15 mg) in light yellow color. $^1$H-NMR (CD$_3$OD) δ values: 3.17 (3 H, s), 3.5–3.7 (4 H, m), 3.8–4.2 (4 H, m), 4.13 (2 H, d), 5.65–5.8 (2 H, m), 6.0–6.15 (1 H, m), 6.93 (1 H, s), 7.20 (1 H, s); MS (EI): m/z 306 (M$^+$)

INVENTIVE EXAMPLE 8
6-Benzylideneamino-5-chloro-2-(4-methyl-1-piperazinyl)benzoxazole A 30 mg portion of 6-amino-5-chloro-2-(4-methyl-1-piperazinyl)benzoxazole was dissolved in 20 ml of anhydrous toluene, and the solution was mixed with 1 ml of benzaldehyde and heated under reflux for 6 hours. The solvent was concentrated under a reduced pressure, and the residual oily matter was mixed with hexane and then the thus formed precipitate was collected by filtration to obtain the title compound (24 mg) in white color.

$^1$H-NMR (CD$_3$OD) δ values: 2.32 (3 H, s), 2.58 (4 H, t), 3.70 (4 H, t), 7.25 (1 H, s), 7.30 (1 H, s), 7.4–7.55 (3 H, m), 7.9–8.0 (2 H, m), 8.48 (1 H, s); MS (EI): m/z 354 (M$^+$)

INVENTIVE EXAMPLE 9
5-Methyl-2-(1-piperazinyl)benzoxazole

A 100 mg portion of 5-methyl-2-mercaptobenzoxazole was suspended in 20 ml of anhydrous toluene, and the suspension was mixed with 150 mg of phosphorus pentachloride and heated under reflux for 1 hour. The reaction solution was cooled in an ice bath and, with stirring, 500 mg of piperazine was added thereto. After 30 minutes of stirring, the ice bath was removed to carry out 1 hour of stirring at room temperature, the reaction solution was mixed with saturated sodium bicarbonate aqueous solution, and then the water layer was washed with ethyl acetate and concentrated under a reduced pressure. Thereafter, the thus obtained mixture was purified by an LH-20 gel column chromatography (chloroform:methanol=1:1) to obtain the title compound (40 mg) in white color.

$^1$H-NMR (DCl) δ values: 2.39 (3 H, s), 3.35 (4 H, t), 4.05 (4 H, t), 3.75 (2 H, d), 7.12 (1 H, d), 7.24 (1 H, s), 7.39 (1 H, s); MS (EI): m/z 217 (M$^+$)

INVENTIVE EXAMPLE 10
6-Amino-5-chloro-2-(1-piperazinyl)benzoxazole a) Using 5-chloro-6-nitro-2-mercaptobenzoxazole, the procedure of Inventive Example 9 was repeated to obtain 5-chloro-6-nitro-2-(1-piperazinyl)benzoxazole.

$^1$H-NMR (CD$_3$OD) δ values: 2.91 (4 H, t), 3.68 (4 H, t), 7.30 (1 H, s), 7.98 (1 H, s); MS (EI): m/z 282 (M$^+$)

b) Using 5-chloro-6-nitro-2-(1-piperazinyl)benzoxazole obtained in the above step (a), the procedure of Inventive Example 5 was repeated to obtain the title compound.

$^1$H-NMR (CD$_3$OD) δ values: 3.08 (4 H, t), 3.63 (4 H, t), 6.82 (1 H, s), 7.09 (1 H, s); MS (EI): m/z 252 (M$^+$)

INVENTIVE EXAMPLE 11
6-Dimethylamino-5-chloro-2-(4-methyl-1-piperaziny)benzoxazole A 40 mg portion of 6-amino-5-chloro-2-(4-methyl-1-piperazinyl)benzoxazole was dissolved in 5 ml of methanol, and the solution was mixed with 1 ml of 1 N hydrochloric acid aqueous solution, 1 ml of formaldehyde and 20 mg of Pd/C catalyst and then, after replacing the atmosphere in the reaction container by hydrogen gas, stirred at room temperature for 4 hours. The catalyst was removed by filtration and the solvent was concentrated to about 1 ml under a reduced pressure. This was adjusted to a pH value of about 7.5 by adding saturated sodium bicarbonate, and the thus precipitated crystals were collected by filtration. Thereafter, the thus collected crystals were dried under a reduced pressure to obtain the title compound (10 mg) in white color.

$^1$H-NMR (CD$_3$OD) δ values: 2.30 (3 H, s), 2.54 (4 H, t), 2.73 (3 H, s), 3.59 (4 H, t), 7.22 (2 H, s); MS (EI): m/z 294 (M$^+$)

INVENTIVE EXAMPLE 12
2-(4-Pyridyl)benzoxazole

A 500 mg portion of pyridine-4-aldehyde was dissolved in 15 ml of acetic acid, and the solution was mixed with 509 mg of o-aminophenol and stirred with heating at 100° C. for 6 hours. The solvent was concentrated under a reduced pressure, and the residual oily matter was mixed with saturated sodium bicarbonate aqueous solution and extracted with ethyl acetate. The organic layer was washed with saturated brine and dried with magnesium sulfate, and then the solvent was evaporated under a reduced pressure. Thereafter, the thus obtained mixture was purified by a silica gel column chromatography (ethyl acetate:hexane=1:1) to obtain the title compound (90 mg) in light yellow color.

$^1$H-NMR (CD$_3$OD) δ values: 7.4–7.5 (2 H, m), 7.64 (1 H, d), 7.83 (1 H, d), 8.10 (2 H, d), 8.81 (2 H, d); MS (EI): m/z 180 (M$^+$)

INVENTIVE EXAMPLE 13
5,7-Dimethyl-2-(1-piperazinyl)benzoxazole

A 50 mg portion of 5,7-dimethyl-2-mercaptobenzoxazole was dissolved in 5 ml of nitromethane, and the solution was mixed with 240 mg of piperazine and heated under reflux for 12 hours. The solvent was concentrated under a reduced pressure, and the residual oily matter was mixed with saturated sodium bicarbonate aqueous solution and extracted with ethyl acetate. The organic layer was washed with saturated brine and dried with magnesium sulfate, and then the solvent was evaporated under a reduced pressure. Thereafter, the thus obtained mixture was purified by a silica gel column chromatography (chloroform:methanol=20:1) to obtain the title compound (35 mg) in white color.

$^1$H-NMR (CD$_3$OD) δ values: 2.24 (3 H, s), 2.28 (3 H, s), 2.86 (4 H, t), 3.54 (4 H, t), 6.59 (1 H, s), 6.82 (1 H, s); MS (EI): m/z 231 (M$^+$)

INVENTIVE EXAMPLE 14
2-(1-Piperazinyl)benzoxazole

Anhydrous piperazine (5.6 g) was dissolved in methylene chloride (100 ml) to which was subsequently added triethylamine (4.5 ml). With cooling in an ice bath, to this was added dropwise 2-chlorobenzoxazole (3.7 ml) in small portions, followed by 45 minutes of stirring. The reaction solution was mixed with water, extracted with methylene chloride and then washed with saturated sodium bicarbonate aqueous solution and saturated brine in that order. The organic layer was dried with magnesium sulfate and the solvent was evaporated under a reduced pressure. Thereafter, the thus obtained mixture was purified by a silica gel column chromatography (methanol) to obtain the title compound 2-(1-piperazinyl)benzoxazole (4.751 g) in the form of yellow crystalline powder.

$^1$H-NMR (CDCl$_3$): δ 2.99 (4 H, t), 3.48 (1 H, s), 3.68 (4 H, t), 7.02 (1 H, dt), 7.16 (1 H, dt), 7.25 (1 H, dd), 7.36 (1 H, dd); ESIMS: m/z 204 (M$^+$+1)

INVENTIVE EXAMPLE 15
2-(4-Piperidyl)benzoxazole

2-Aminophenol (200 mg) and 4-piperidinecarboxylic acid (236 mg) were mixed with polyphosphoric acid (1 g) and stirred with heating at 180° C. for 2 hours. After cooling to room temperature, the reaction was stopped by adding water. The filtrate was adjusted to pH 12 with 50% potassium hydroxide aqueous solution and then extracted with methylene chloride. The organic layer was washed with saturated brine and dried with magnesium sulfate, and then the solvent was evaporated under a reduced pressure to obtain the title compound 2-(4-piperidyl)benzoxazole (311.5 mg).

$^1$H-NMR (CDCl$_3$): δ 1.89 (2 H, ddd), 2.16 (2 H, dd), 2.79 (2 H, dt), 3.20 (1 H, t), 3.23 (1 H, t), 3.05–3.15 (1 H, m), 7.27–7.32 (2 H, m), 7.46–7.52 (1 H, m), 7.66–7.72 (1 H, m); EIMS: m/z 202 (M$^+$)

INVENTIVE EXAMPLE 16
2-(4-Piperidyl)-5-methylbenzoxazole

2-Amino-4-methylphenol (400 mg) and 4-piperidinecarboxylic acid (420 mg) were mixed with polyphosphoric acid (2 g) and stirred with heating at 180° C. for 2 hours. After cooling to room temperature, the reaction was stopped by adding water. The filtrate was adjusted to pH 12 with 50% potassium hydroxide aqueous solution and then extracted with methylene chloride. The organic layer was washed with saturated brine and dried with magnesium sulfate, and then the solvent was evaporated under a reduced pressure to obtain the title compound 2-(4-piperidyl)-5-methylbenzoxazole (586 mg).

$^1$H-NMR (CDCl$_3$): δ 1.87 (4 H, t), 2.14 (1 H, d), 2.46 (3 H, s), 2.79 (2 H, t), 3.04–3.14 (1 H, m), 3.21 (2 H, d), 7.10 (1 H, d), 7.35 (1 H, d), 7.47 (1 H, s); EIMS: m/z 216 (M$^+$)

INVENTIVE EXAMPLE 17
2-(4-Methyl-1-piperazinyl)-5-methylbenzoxazole

Phosphorus pentachloride (227 mg) was dissolved in anhydrous toluene (3 ml), the resulting solution was mixed with 2-mercapto-5-methylbenzoxazole (150 mg) which has been obtained in the same manner as described in Reference Example 1, and the mixture was then stirred with heating at 100° C. for 2 hours. With cooling in an ice bath, to this was added dropwise N-methylpiperazine (1 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica.gel column chromatography (methylene chloride:methanol=10:1) to obtain the title compound 2-(4-methyl-1-piperazinyl)-5-methylbenzoxazole (188 mg).

$^1$H-NMR (CDCl$_3$): δ 2.35 (3 H, s), 2.39 (3 H, s), 2.52 (4 H, t), 3.71 (4 H, t), 6.82 (1 H, dd), 7.11 (1 H, d), 7.15 (1 H, s); EIMS: m/z 231 (M$^+$)

INVENTIVE EXAMPLE 18
2-(4-Methyl-1-piperazinyl)-6-methylbenzoxazole

Phosphorus pentachloride (302 mg) was dissolved in anhydrous toluene (4 ml), the resulting solution was mixed with 2-mercapto-6-methylbenzoxazole (200 mg) which has been obtained in the same manner as described in Reference Example 1, and the mixture was then stirred with heating at 100° C. for 2 hours. With cooling in an ice bath, to this was added dropwise N-methylpiperazine (1.34 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol=10:1) to obtain the title compound 2-(4-methyl-1-piperazinyl)-6-methylbenzoxazole (166 mg).

$^1$H-NMR (CDCl$_3$): δ 2.35 (3 H, s), 2.40 (3 H, s), 2.52 (4 H, t), 3.70 (4 H, t), 6.97 (1 H, d), 7.07 (1 H, s), 7.23 (1 H, d); EIMS: m/z 231 (M$^+$)

INVENTIVE EXAMPLE 19
2-(4-Methyl-1-piperazinyl)-7-methylbenzoxazole

Phosphorus pentachloride (454 mg) was dissolved in anhydrous toluene (6 ml), the resulting solution was mixed with 2-mercapto-7-methylbenzoxazole (300 mg) which has been obtained in the same manner as described in Reference Example 1, and the mixture was then stirred with heating at 100° C. for 2 hours. With cooling in an ice bath, to this was added dropwise N-methylpiperazine (2.0 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol=10:1) to obtain the title compound 2-(4-methyl-1-piperazinyl)-7-methylbenzoxazole (392 mg).

$^1$H-NMR (CDCl$_3$): δ 2.36 (3 H, s), 2.42 (3 H, s), 2.53 (4 H, t), 3.73 (4 H, t), 6.83 (1 H, d), 7.06 (1 H, t), 7.19 (1 H, d); EIMS: m/z 231 (M$^+$)

INVENTIVE EXAMPLE 20
2-(4-Methyl-1-piperazinyl)-5,7-dichlorobenzoxazole

Phosphorus pentachloride (454 mg) was dissolved in anhydrous toluene (6 ml), the resulting solution was mixed with 2-mercapto-5,7-dichlorobenzoxazole (400 mg) which has been obtained in the same manner as described in Reference Example 1, and the mixture was then stirred with heating at 100° C. for 2 hours. With cooling in an ice bath, to this was added dropwise N-methylpiperazine (2.0 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol= 10:1) to obtain the title compound 2-(4-methyl-1-piperazinyl)-5,7-dichlorobenzoxazole (89.9 mg).

$^1$H-NMR (CDCl$_3$): δ 2.36 (3 H, s), 2.53 (4 H, t), 3.75 (4 H, t), 7.00 (1 H, d), 7.18 (1 H, d); EIMS: m/z 285 (M$^+$), 287 (M$^+$+2), 289 (M$^+$+4)

INVENTIVE EXAMPLE 21

2-(4-Methyl-1-piperazinyl)naphtho[1,2-d]oxazole

Phosphorus pentachloride (498 mg) was dissolved in anhydrous toluene (8 ml), the resulting solution was mixed with 2-mercaptonaphtho[1,2-d]oxazole (400 mg) which has been obtained in the same manner as described in Reference Example 1, and the mixture was then stirred with heating at 100° C. for 2 hours. With cooling in an ice bath, to this was added dropwise N-methylpiperazine (2.2 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol=10:1) to obtain the title compound 2-(4-methyl-1-piperazinyl)naphtho[1,2-d]oxazole (94.9 mg).

$^1$H-NMR (CDCl$_3$): δ 2.38 (3 H, s), 2.57 (4 H, t), 3.80 (4 H, t), 7.44 (1 H, t), 7.47–7.55 (3 H, m), 7.88 (1 H, d), 8.32 (1 H, d); EIMS: m/z 267 (M$^+$)

INVENTIVE EXAMPLE 22

2-(4-Methyl-1-piperazinyl)-5-aminobenzoxazole a) Phosphorus pentachloride (1.37 g) was dissolved in anhydrous toluene (18 ml), the resulting solution was mixed with 2-mercapto-5-nitrobenzoxazole (900 mg) which has been obtained in the same manner as described in Reference Example 1, and the mixture was then stirred with heating at 100° C. for 3 hours. With cooling in an ice bath, to this was added dropwise N-methylpiperazine (6.09 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol=10:1) to obtain 2-(4-methyl-1-piperazinyl)-5-nitrobenzoxazole (56.1 mg) in the form of yellow crystalline powder.

$^1$H-NMR (CDCl$_3$): δ 2.37 (3 H, s), 2.56 4 H, t), 3.71 (4 H, t), 7.68 (1 H, d), 7.96 (1 H, d), 8.34 (1 H, s); EIMS: m/z 262 (M$^+$)

b) 2-(4-Methyl-1-piperazinyl)-5-nitrobenzoxazole (26 mg) obtained in the above step (a) was dissolved in acetic acid (2 ml), and the solution was mixed with 10% palladium-carbon (10 mg) and stirred overnight at room temperature in an atmosphere of hydrogen. Thereafter, the reaction solution was filtered through celite, and then the solvent was evaporated under a reduced pressure to obtain the title compound 2-(4-methyl-1-piperazinyl)-5-aminobenzoxazole (6.3 mg).

$^1$H-NMR (CDCl$_3$): δ 2.36 (3 H, s), 2.56 (4 H, t), 3.64 (4 H, t), 6.49 (1 H, dd), 6.91 (1 H, d), 7.33 (1 H, d); EIMS: m/z 233 (M$^+$+1)

INVENTIVE EXAMPLE 23

2-(4-Methyl-1-piperazinyl)-6-aminobenzoxazole a) Phosphorus pentachloride (764 mg) was dissolved in anhydrous toluene (9 ml), the resulting solution was mixed with 2-mercapto-6-nitrobenzoxazole (600 mg) which has been obtained in the same manner as described in Reference Example 1, and the mixture was then stirred with heating at 100° C. for 3 hours. With cooling in an ice bath, to this was added dropwise N-methylpiperazine (3.4 ml). After 20 minutes of stirring, the thus obtained mixture was extracted with ethyl acetate, and the organic layer was washed with saturated sodium bicarbonate aqueous solution and saturated brine in that order. After drying with magnesium sulfate, the solvent was evaporated under a reduced pressure, and the resulting residue was purified by a silica gel column chromatography (methylene chloride:methanol=20:1) to obtain 2-(4-methyl-1-piperazinyl)-6-nitrobenzoxazole (668.9 mg) in the form of yellow crystalline powder.

$^1$H-NMR (CDCl$_3$): δ 2.37 (3 H, s), 2.56 (4 H, t), 3.81 (4 H, t), 7.32 (1 H, d), 8.14 (1 H, d), 8.19 (1 H, dd); EIMS: m/z 262 (M$^+$)

b) 2-(4-Methyl-1-piperazinyl)-6-nitrobenzoxazole obtained in the above step (a) was dissolved in acetic acid (2 ml), and the solution was mixed with 10% palladium-carbon (10 mg) and stirred overnight at room temperature in an atmosphere of hydrogen. Thereafter, the reaction solution was filtered through celite and then the solvent was evaporated under a reduced pressure to obtain the title compound 2-(4-methyl-1-piperazinyl)-6-aminobenzoxazole (35 mg).

$^1$H-NMR (CDCl$_3$): δ 2.36 (3 H, s), 2.57 (4 H, t), 3.69 (4 H, t), 4.30 (1 H, brs), 6.55 (1 H, dt), 6.67 (1 H, t), 7.15 (1 H, dd); EIMS: m/z 233 (M$^+$+1)

INVENTIVE EXAMPLE 24

2-(4-Methyl-1-piperazinyl)-5-trifluoromethylbenzoxazole

2-Mercapto-5-trifluoromethylbenzoxazole (200 mg) which has been obtained in the same manner as described in Reference Example 1 was dissolved in chloroform (10 ml), and the solution was mixed with N-methylpiperazine (0.5 ml) and heated overnight under reflux. The solvent was evaporated under a reduced pressure, the resulting residue was mixed with water and then the thus precipitated solid matter was collected by filtration to obtain the title compound 2-(4-methyl-1-piperazinyl)-5-trifluoromethylbenzoxazole (134 mg).

$^1$H-NMR (CDCl$_3$): δ 2.36 (3 H, s), 2.54 (4 H, t), 3.75 (4 H, t), 7.30 (2 H, d), 7.57 (1 H, s); LCMS: m/z 286 (M$^+$+1)

INVENTIVE EXAMPLE 25

1-Allyl-1-methyl-4-(5-methylbenzoxazol-2-yl) piperazinium bromide 2-(4-Methyl-1-piperazinyl)-5-methylbenzoxazole (21 mg) obtained in Inventive Example 17 was dissolved in N,N-dimethylformamide (1 ml), and the solution was mixed with allyl bromide (0.15 ml) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(5-methylbenzoxazol-2-yl)piperazinium bromide (28 mg).

$^1$H-NMR (CD$_3$OD): δ 2.43 (3 H, s), 3.28 (3 H, s), 3.60–3.80 (4 H, m), 3.98–4.10 (2 H, m), 4.14–4.30 (4 H, m), 5.80–5.90 (2 H, m), 6.12–6.25 (1 H, m), 6.99 (1 H, d), 7.21 (1 H, s), 7.30 (1 H, d); LCMS: m/z 272 (M$^+$)

INVENTIVE EXAMPLE 26
1-Allyl-1-methyl-4-(5-trifluoromethylbenzoxazol-2-yl)piperazinium bromide 2-(4-Methyl-1-piperazinyl)-5-trifluoromethylbenzoxazole (29 mg) obtained in Inventive Example 25 was dissolved in N,N-dimethylformamide (1 ml), and the solution was mixed with allyl bromide (85 μl) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(5-trifluoromethylbenzoxazol-2-yl)piperazinium bromide (30 mg).

$^1$H-NMR (CD$_3$OD): δ 3.29 (3 H, s), 3.65–3.80 (4 H, m), 4.05–4.15 (2 H, m), 4.22–4.30 (4 H, m), 5.80–5.90 (2 H, m), 6.10–6.30 (1 H, m), 7.49 (1 H,d), 7.61 (1 H, d), 7.65 (1 H, s); LCMS: m/z 326 (M$^+$)

INVENTIVE EXAMPLE 27
1-Allyl-1-methyl-4-(6-methylbenzoxazol-2-yl)piperazinium bromide 2-(4-Methyl-1-piperazinyl)-6-methylbenzoxazole (15 mg) obtained in Inventive Example 18 was dissolved in N,N-dimethylformamide (0.5 ml), and the solution was mixed with allyl bromide (51 μl) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(6-methylbenzoxazol-2-yl)piperazinium bromide (15 mg).

$^1$H-NMR (CD$_3$OD): δ 2.45 (3 H, s), 3.27 (3 H, s), 3.60–3.80 (4 H, m), 3.95–4.10 (2 H, m), 4.10–4.30 (4 H, m), 5.80–5.90 (2 H, m), 6.10–6.25 (1 H, m), 7.10 (1 H, d), 7.26 (1 H, s), 7.27 (1 H, d); LCMS: m/z 272 (M$^+$)

INVENTIVE EXAMPLE 28
1-Allyl-1-methyl-4-(7-methylbenzoxazol-2-yl)piperazinium bromide 2-(4-Methyl-1-piperazinyl)-7-methylbenzoxazole (23 mg) obtained in Inventive Example 19 was dissolved in N,N-dimethylformamide (1 ml), and the solution was mixed with allyl bromide (85 μl) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(7-methylbenzoxazol-2-yl)piperazinium bromide (34 mg).

$^1$H-NMR (CD$_3$OD): δ 2.49 (3 H, s), 3.28 (3 H, s), 3.60–3.80 (4 H, m), 4.00–4.15 (2 H, m), 4.15–4.30 (4 H, t), 5.80–6.00 (2 H, m), 6.10–6.30 (1 H, m), 6.99 (1 H, d), 7.16 (1 H, t), 7.20 (1 H, d); FABMS: m/z 272 (M$^+$)

INVENTIVE EXAMPLE 29
1-Allyl-1-methyl-4-(5,7-dichlorobenzoxazol-2-yl)piperazinium bromide 2-(4-Methyl-1-piperazinyl)-5,7-dichlorobenzoxazole (20 mg) obtained in Inventive Example 20 was dissolved in N,N-dimethylformamide (1 ml), and the solution was mixed with allyl bromide (59 μl) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(5,7-dichlorobenzoxazol-2-yl)piperazinium bromide (27 mg).

$^1$H-NMR (CD$_3$OD): δ 3.28 (3 H, s), 3.65–3.77 (4 H, m), 4.05–4.15 (2 H, m), 4.20–4.30 (4 H, m), 5.80–5.90 (2 H, m), 6.12–6.25 (1 H, m), 7.23 (1 H, d), 7.33 (1 H, d); LCMS: m/z 326 (M$^+$)

INVENTIVE EXAMPLE 30
1-Allyl-1-methyl-4-(naphtho[1,2-d]benzoxazol-2-yl)piperazinium bromide 2-(4-Methyl-1-piperazinyl)naphtho[1,2-d]oxazole (27 mg) obtained in Inventive Example 21 was dissolved in N,N-dimethylformamide (1 ml), and the solution was mixed with allyl bromide (85 μl) and stirred overnight at room temperature. The solvent was evaporated under a reduced pressure, the resulting residue was mixed with ethyl acetate and then the thus precipitated solid matter was collected by filtration to obtain the title compound 1-allyl-1-methyl-4-(naphtho[1,2-d]benzoxazol-2-yl)piperazinium bromide (33 mg).

$^1$H-NMR (CD$_3$OD): δ 3.30 (3 H, s), 3.75–3.80 (4 H, m), 4.18–4.20 (2 H, m), 4.20–4.32 (4 H, m), 5.80–5.90 (2 H, m), 6.15–6.30 (1 H, m), 7.52 (1 H, dt), 7.61 (1 H, dt), 7.66 (1 H, d), 7.71 (1 H, d), 7.99 (1 H, d), 8.32 (1 H, d); FABMS: m/z 308 (M$^+$)

INVENTIVE EXAMPLE 31
5-Chloro-7-methyl-2-(4-methyl-1-piperazinyl)benzoxazole 5-Chloro-7-methyl-2-mercaptobenzoxazole (200 mg) was dissolved in chloroform (20 ml), N-methylpiperazine (0.55 ml) was added dropwise to the solution and then the mixture was stirred with heating for 3 days. After evaporation of the solvent, the thus obtained mixture was purified by a silica gel column chromatography (methylene chloride:methanol=20:1) to obtain the title compound 5-chloro-7-methyl-2-(4-methyl-1-piperazinyl)benzoxazole (270 mg).

$^1$H-NMR (CDCl$_3$): δ 2.36 (3 H, s), 2.37 (3 H, s), 2.53 (4 H, t), 3.72 (4 H, t), 6.81 (1 H, d), 7.14 (1 H, d) SIMS: m/z 266 (M$^+$+1), 268 (M$^+$+3)

INVENTIVE EXAMPLE 32
5-Chloro-2-(1-piperidyl)benzoxazole

2-Amino-4-chlorophenol (400 mg) and 4-piperidinecarboxylic acid (360 mg) were mixed with polyphosphate (2 g) in xylene (30 ml) and stirred with heating at 180° C. for 2 hours. After cooling to room temperature, the reaction was stopped by adding water. The filtrate was adjusted to pH 12 with 50% potassium hydroxide aqueous solution and extracted with methylene chloride. The organic layer was washed with saturated brine and dried with magnesium sulfate, and then the solvent was evaporated under a reduced pressure to obtain the title compound 5-chloro-2-(1-piperidyl)benzoxazole (218 mg).

$^1$H-NMR (CDCl$_3$): δ 1.60–1.75 (2 H, m), 1.99 (2 H, d), 2.61 (2 H, t), 2.99 (2 H, d), 3.00–3.20 (1 H, m), 4.02 (1 H, brs), 7.39 (1 H, dd), 7.72 (1 H, d), 7.81 (1 H, d) EIMS: m/z 236 (M$^+$), 238 (M$^+$+2)

INVENTIVE EXAMPLE 33
5-Chloro-6,7-dimethyl-2-(4-methyl-1-piperazinyl)benzoxazole 5-Chloro-6,7-dimethyl-2-mercaptobenzoxazole (200 mg) was dissolved in chloroform (20 ml), N-methylpiperazine (1.54 ml) was added dropwise to the solution and then the mixture was stirred with heating for 29 hours. After evaporation of the solvent, the thus obtained mixture was purified by a silica gel column chromatography (methylene chloride:methanol=20:1) to obtain the title compound 5-chloro-6,7-dimethyl-2-(4-methyl-1-piperazinyl)benzoxazole (260 mg).

$^1$H-NMR (CDCl$_3$): δ 2.33 (3 H, s), 2.35 (3 H, s), 2.36 (3 H, s), 2.54 (4 H, t), 3.72 (4 H, t), 7.20 (1 H, s) SIMS: m/z 280 (M$^+$+1), 282 (M$^+$+3)

INVENTIVE EXAMPLE 34
5,7-Dichloro-6-methyl-2-(4-methyl-1-piperazinyl)benzoxazole 5,7-Dichloro-6-methyl-2-mercaptobenzoxazole (200 mg) was dissolved in chloroform (20 ml), N-methylpiperazine (0.94 ml) was added dropwise to the solution and then the mixture was stirred with heating for 29 hours. After evaporation of the solvent, the thus obtained mixture was purified by a silica gel column chromatography (methylene chloride:methanol=20:1) to obtain the title compound 5,7-dichloro-6-methyl-2-(4-methyl-1-piperazinyl)benzoxazole (163 mg).

$^1$H-NMR (CDCl$_3$): δ 2.36 (3 H, s), 2.47 (3 H, s), 2.53 (4 H, t), 3.74 (4 H, t), 7.26 (1 H, s) EIMS: m/z 299 (M+−1)

INVENTIVE EXAMPLE 35
5-Methyl-2-(4-methyl-1-homopiperazinyl)benzoxazole

5-Methyl-2-mercaptobenzoxazole (200 mg) was dissolved in chloroform (20 ml), N-methylhomopiperazine (1.24 ml) was added dropwise to the solution and then the mixture was stirred with heating for 2 days. After evaporation of the solvent, the thus obtained mixture was purified by a silica gel column chromatography (methylene chloride:methanol=10:1) to obtain the title compound 5-methyl-2-(4-methyl-1-homopiperazinyl)benzoxazole (124 mg).

$^1$H-NMR (CDCl$_3$): δ 2.00–2.10 (2 H, m), 2.64 (2 H, t), 2.76 (2 H, t), 3.80 (2 H, t), 3.86 (2 H, t), 6.79 (1 H, d), 7.11 (1 H, d), 7.14 (1 H, s); SIMS: m/z 246 (M$^+$+1)

INVENTIVE EXAMPLE 36
5,7-Dimethyl-2-(4-methyl-1-homopiperazinyl)benzoxazole 5,7-Dimethyl-2-mercaptobenzoxazole (220 mg) was dissolved in chloroform (20 ml), N-methylhomopiperazine (0.76 ml) was added dropwise to the solution and then the mixture was stirred with heating for 2 days. After evaporation of the solvent, the thus obtained mixture was purified by a silica gel column chromatography (methylene chloride:methanol=20:1) to obtain the title compound 5,7-dimethyl-2-(4-methyl-1-homopiperazinyl)benzoxazole (110 mg).

$^1$H-NMR (CDCl$_3$): δ 2.00–2.10 (2 H, m), 2.34 (3 H, s), 2.36 (3 H, s), 2.39 (3 H, s), 2.60–2.65 (2 H, m), 3.76–3.87 (4 H, m), 6.62 (1 H, s), 6.98 (1 H, s); SIMS: m/z 260 (M$^+$+1)

INVENTIVE EXAMPLE 37
5-Chloro-7-methyl-2-(4-methyl-1-homopiperazinyl)benzoxazole 5-Chloro-7-methyl-2-mercaptobenzoxazole (200 mg) was dissolved in toluene (10 ml), N-methylhomopiperazine (1.24 ml) was added dropwise to the solution and then the mixture was stirred with heating for 1 hour. After evaporation of the solvent, the thus obtained mixture was purified by a silica gel column chromatography (methylene chloride:methanol=10:1) to obtain the title compound 5-chloro-7-methyl-2-(4-methyl-1-homopiperazinyl)benzoxazole (266 mg).

$^1$H-NMR (CDCl$_3$): δ 2.00–2.07 (2 H, m), 2.37 (3 H, s), 2.40 (3 H, s), 2.63 (2 H, t), 2.74 (2 H, t), 3.79 (2 H, t), 3.85 (2 H, t), 6.78 (1 H, d), 7.13 (1 H, d); SIMS: m/z 280 (M$^+$+1), 282 (M$^+$+3)

INVENTIVE EXAMPLE 38
5-Chloro-7-ethyl-2-(4-methyl-1-homopiperazinyl)benzoxazole 5-Chloro-7-ethyl-2-mercaptobenzoxazole (200 mg) was dissolved in toluene (10 ml), N-methylhomopiperazine (1.17 ml) was added dropwise to the solution and then the mixture was stirred with heating for 5 hours. After evaporation of the solvent, the thus obtained mixture was purified by a silica gel column chromatography (methylene chloride:methanol=10:1) to obtain the title compound 5-chloro-7-ethyl-2-(4-methyl-1-homopiperazinyl)benzoxazole (211 mg).

$^1$H-NMR (CDCl$_3$): δ 1.29 (3 H, t), 2.00–2.10 (2 H, m), 2.41 (3 H, s), 2.62–2.66 (2 H, m), 2.72–2.80 (4 H, m), 3.79 (2 H, t), 3.83–3.88 (2 H, m), 6.80 (1 H, d), 7.14 (1 H, d) SIMS: m/z 294 (M$^+$+1), 296 (M$^+$+3)

INVENTIVE EXAMPLE 39
5-Chloro-6-methyl-2-(4-methyl-1-homopiperazinyl)benzoxazole 5-Chloro-6-methyl-2-mercaptobenzoxazole (200 mg) was dissolved in chloroform (20 ml), N-methylhomopiperazine (1.24 ml) was added dropwise to the solution and then the mixture was stirred with heating for 2 days. After evaporation of the solvent, the thus obtained mixture was purified by a silica gel column chromatography (methylene chloride:methanol=20:1) to obtain the title compound 5-chloro-6-methyl-2-(4methyl-1-homopiperazinyl)benzoxazole (183 mg).

$^1$H-NMR (CDCl$_3$): δ 2.00–2.07 (2 H, m), 2.37 (3 H, s), 2.40 (3 H, s), 2.63 (2 H, t), 2.74 (2 H, t), 3.79 (2 H, t), 3.85 (2 H, t), 6.78 (1 H, d), 7.13 (1 H, d); FABMS: m/z 280 (M$^+$+1), 282 (M$^+$+3)

INVENTIVE EXAMPLE 40
2-(4-Methyl-1-homopiperazinyl)naphtho[1,2-d]oxazole

2-Mercapto-naphtho[1,2-d]oxazole (200 mg) was dissolved in chloroform (20 ml), N-methylhomopiperazine (2.48 ml) was added dropwise to the solution and then the mixture was stirred with heating for 2 days. After evaporation of the solvent, the thus obtained mixture was purified by a silica gel column chromatography (methylene chloride:methanol=10:1) to obtain the title compound 2-(4-methyl-1-homopiperazinyl)naphtho[1,2-d]oxazole (137 mg).

$^1$H-NMR (CDCl$_3$): δ 2.04–2.12 (2 H, m), 2.41 (3 H, s), 2.65 (2 H, t), 2.79 (2 H, t), 3.94 (2 H, t), 3.89 (2 H, t), 7.43 (1 H, t), 7.50 (2 H, s), 7.52 (1 H, t), 7.88 (1 H, d), 8.33 (1 H, d); EIMS: m/z 281 (M$^+$)

INVENTIVE EXAMPLE 41
5-Chloro-2-(4-methyl-1-homopiperazinyl)benzoxazole

5-Chloro-2-mercaptobenzoxazole (1 g) was dissolved in toluene (50 ml), N-methylhomopiperazine (3.3 ml) was added dropwise to the solution and then the mixture was stirred with heating for 2 hours. After evaporation of the solvent, the thus obtained mixture was purified by a silica gel column chromatography (methylene chloride:methanol=20:1) to obtain the title compound 5-chloro-2-(4-methyl-1-homopiperazinyl)-benzoxazole (882 mg).

$^1$H-NMR (CDCl$_3$): δ 2.03–2.10 (2 H, m), 2.42 (3 H, s), 2.65–2.70 (2 H, m), 2.76–2.82 (2 H, m), 3.75–3.88 (4 H, m), 6.94 (1 H, d), 7.13 (1 H, d), 7.30 (1 H, s); EIMS: m/z 265 (M$^+$)

INVENTIVE EXAMPLE 42
5-Chloro-6-amino-2-(4-methyl-1-homopiperazinyl)benzoxazole a) Using 5-chloro-6-nitro-2-mercaptobenzoxazole, the procedure of Inventive Example 41 was repeated to obtain 5-chloro-6-nitro-2-(4-methyl-1-homopiperazinyl)benzoxazole.

b) A 50 mg portion of 5-chloro-6-nitro-2-(4-methyl-1-homopiperazinyl)benzoxazole was dissolved in 15 ml of methanol, and the resulting solution was mixed with 5 ml of 1 N hydrochloric acid aqueous solution and 30 mg of Pd/C catalyst and, after replacing the atmosphere in the reaction container by hydrogen gas, stirred at room temperature for 15 hours. The catalyst was removed by filtration and the solvent was concentrated under a reduced pressure. The thus remained oily matter was mixed with 5 ml of 1 N hydrochloric acid and washed with ethyl acetate. This was adjusted to pH 8 by adding saturated sodium bicarbonate, and the thus precipitated crystals were collected by filtration to obtain the title compound (16 mg).

$^1$H-NMR (CDCl$_3$): β 2.02–2.13 (2 H, m), 2.42 (3 H, s), 2.60–2.70 (2 H, m), 2.74–2.84 (2 H, m), 3.77–3.95 (4 H, m), 6.82 (1 H, s), 7.29 (1 H, s); MS (El): m/z 280 (M$^+$)

INVENTIVE EXAMPLE 43

5,7-Dimethyl-2-(1,4-diazacyclooctanyl)benzoxazole 5,7-Dimethyl-2-mercapto-benzoxazole (109 mg) was dissolved in toluene (6 ml), and the solution was mixed with 1,4-diazacyclooctane (1.93 g) which has been obtained in accordance with the method described in Carib. J. Sci., 14, 77 (1974) and then stirred with heating for 3 hours. After evaporation of the solvent, the thus obtained mixture was purified by a silica gel column chromatography (methylene chloride:methanol=5:1) to obtain the title compound 5,7-dimethyl-2-(1,4-diazacyclooctanyl)benzoxazole (271 mg).

$^1$H-NMR (CDCl$_3$): δ 1.88 (4 H, quin), 2.36 (3 H, s), 2.38 (3 H, s), 3.24 (2 H, t), 3.41 (2 H, t), 3.88 (2 H, t), 4.10 (2 H, t), 6.67 (1 H, s), 7.00 (1 H, s); SIMS: m/z 260 (M$^+$+1)

INVENTIVE EXAMPLE 44

5,7-Dimethyl-2-(4-methyl-1,4-diazacyclooctanyl)benzoxazole 5,7-Dimethyl-2-(1,4-diazacyclooctanyl)benzoxazole (135 mg) was dissolved in methanol (3 ml), and the solution was mixed with 37% formaldehyde solution (1 ml) and 1 N hydrochloric acid (0.5 ml). This was further mixed with 10% palladium-carbon (10 mg) and stirred overnight in an atmosphere of hydrogen. After removing the catalyst by celite filtration, the filtrate was washed with ethyl acetate and then the solvent was evaporated. The thus obtained residue was extracted with 1 N hydrochloric acid and ethyl acetate, and the resulting water layer was adjusted to pH 8 with potassium carbonate and extracted with methylene chloride. The organic layer was dried with magnesium sulfate and the solvent was evaporated to obtain the title compound 5,7-dimethyl-2-(4-methyl-1,4-diazacyclooctanyl)benzoxazole (50 mg).

$^1$H-NMR (CDCl$_3$): δ 1.60–1.70 (2 H, m), 1.92 (2 H, quin), 2.35 (3 H, s), 2.37 (3 H, s), 2.44 (3 H, s), 2.55–2.65 (2 H, m), 2.75–2.90 (2 H, m), 3.70–3.76 (2 H, m), 3.82 (2 H, t), 6.61 (1 H, s), 6.98 (1 H, s); SIMS: m/z 274 (M++1)

FORMULATON EXAMPLE 1

Preparation of Tablets

The compound of Inventive Example 13 (10.0 g) was mixed with lactose (85.5 g), hydroxypropyl cellulose HPC-SL (2.0 g), hydroxypropyl cellulose L-HPC, LH-22 (2.0 g) and purified water (9.0 g), the resulting mixture was subjected to granulation, drying and grading, and the thus obtained granules were mixed with magnesium stearate (0.5 g) and subjected to tablet making, thereby obtaining tablets containing 10 mg per tablet of the compound of Inventive Example 13.

FORMULATIN EXAMPLE 2

Preparation of Fine Subtilaes

The compound of Inventive Example 13 (10.0 g) was mixed with lactose (960 g), hydroxypropyl cellulose HPC-SL (20.0 g) and purified water (90 g), the resulting mixture was subjected to granulation, drying, grading and screening and then mixed with magnesium stearate (10.0 g), thereby obtaining fine subtilaes containing 10 mg per 1.0 g of the compound of Inventive Example 13.

TEST EXAMPLE 1

Toxicity Test

The compound of Inventive Example 13 or 28 of the present invention was dissolved in water and orally administered to five-week-old male mice (5 animals). No mortal case was found with the dose of 300 mg/kg of the compound of Inventive Example 13 or 28.

TEST EXAMPLE 2

5-HT$_3$ Receptor Activating Action Test

Of the novel and known benzoxazole compounds according to the present invention, typical compounds and the compounds disclosed in JP-A-6-345744, namely 5-methoxy-2-(4-methyl-1-piperazinyl)benzoxazole (A) and 2-(4-methyl-1-piperazinyl)naphtho[2,3-d]oxazole (B), were measured for their serotonin 5-HT$_3$ receptor antagonism and serotonin 5-HT$_3$ receptor activating action by the following method, with the results shown in Table 1. Test compounds of the present invention are shown by the Inventive Example numbers.

Longitudinal muscle samples of about 20 mm were prepared from the ileum of Hartley male guinea pigs (500 to 800 g). Each of the thus prepared samples was hung down in a Magnus tube with a resting tension of about 0.5 g to measure the isometric contraction reaction. Serotonin 5-HT was applied with a concentration of from 0.1 to 30 μM to the sample which has been subjected twice in advance to 1 hour of treatment with 0.3 μM serotonin 5-HT to effect desensitization of serotonin 5-HT$_4$ receptor. When the concentration-dependent contraction reaction mediated by the serotonin 5-HT$_3$ receptor was observed in this manner, the maximum reaction was found at 10 μM.

The i.a. value was expressed as the ratio of the maximum reaction of each compound when the maximum contraction reaction obtained by 10 μM of serotonin 5-HT was defined as 1. The pD$_2$ value was expressed as the negative logarithmic value of concentration (molar concentration) by which 50% of the maximum contraction reaction of each test compound can be obtained. Also, antagonism of each test compound against the serotonin 5-HT$_3$ receptor was calculated as the inhibition ratio of the contraction obtained by applying 10 μM of serotonin 5-HT (manufactured by Sigma) to a sample which has been treated with 10 mM of each test sample to the contraction obtained by applying 10 μM of serotonin 5-HT to the sample before treatment.

TABLE 1

| Example No. | Antagonism (10 μM, %) | Activation Action | |
|---|---|---|---|
| | | i.a. | pD$_2$ |
| 1 | 92 | 0.55 | 6.40 |
| 2 | 90 | 0.57 | 6.65 |
| 5 | 95 | 0.59 | 6.17 |
| 7 | 67 | 0.94 | 6.50 |
| 10 | 88 | 0.69 | 6.17 |
| 13 | 100 | 0.18 | 7.00 |
| 14 | 75 | 0.59 | 5.74 |
| 16 | 82 | 0.24 | 6.21 |
| 21 | 85 | 0.26 | 6.30 |
| 25 | 86 | 0.79 | 6.15 |
| 31 | 85 | 0.24 | 6.70 |

TABLE 1-continued

| Example No. | Antagonism (10 μM, %) | Activation Action i.a. | pD$_2$ |
|---|---|---|---|
| 36 | 96 | 0.28 | 7.20 |
| 37 | 98 | 0.15 | 7.70 |
| 39 | 89 | 0.21 | 7.00 |
| 40 | 89 | 0.21 | 7.10 |
| A | 34 | — | — |
| B | 85 | 0.45 | 5.40 |

The compound A is possessed of serotonin 5-HT$_3$ receptor antagonism but does not have serotonin 5-HT$_3$ receptor activating action. Also, the compound B has serotonin 5-HT$_3$ receptor antagonism, but its serotonin 5-HT$_3$ receptor activating action is weak in comparison with the compounds of the present invention. On the contrary, it was confirmed that the novel and known benzoxazole derivatives of the present invention have excellent serotonin 5-HT$_3$ receptor partial activation function having strong serotonin 5-HT$_3$ receptor activating action in addition to the serotonin 5-HT$_3$ receptor antagonism.

The benzoxazole derivatives of the present invention are useful as serotonin 5-HT$_3$ receptor partial activators.

Thus, as has been described in the foregoing, the benzoxazole derivatives of the present invention are possessed of serotonin 5-HT$_3$ receptor partial activation function having both serotonin 5-HT$_3$ receptor antagonizing and activating actions. The benzoxazole compounds of the present invention are useful as serotonin 5-HT$_3$ receptor partial activators not only for the inhibition of emesis caused by the use of cisplatin and the like carcinostatic agents or by radiation treatments and for the prevention and treatment of difficulty of gastrointestinal moving, irritable colon syndrome and the like, but also for the treatment of headache, neuralgia, anxiety, depression, psychosis and the like. They are particularly useful in the prevention and treatment of difficulty of gastrointestinal moving and irritable colon syndrome as an antidiarrheal drug which does not cause constipation as a side effect.

While the invention has been described in detail and with reference to specific embodiments thereof, it will be apparent to one skilled in the art that various changes and modifications can be made therein without departing from the spirit and scope thereof.

What is claimed is:

1. A compound represented by formula (2):

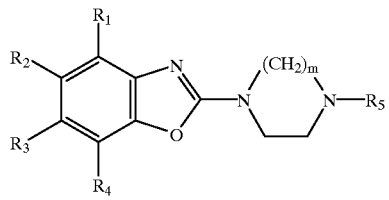

wherein R$_1$ to R$_4$ are the same or different from one another and each represents a hydrogen atom, a halogen atom, a substituted or unsubstituted lower alkyl group, a substituted or unsubstituted lower alkenyl group or a substituted or unsubstituted amino group, or two groups of R$_1$ and R$_2$ are linked together to form a benzene ring and R$_3$ and R$_4$ are hydrogen atoms, with the proviso that compounds in which all of R$_1$ to R$_4$ are hydrogen atoms are excluded; R$_5$ represents a hydrogen atom, and m is an integer of 1 to 4, in which said lower alkyl group means a straight or branched C$_1$–C$_4$ alkyl group, said lower alkenyl group means a straight or branched C$_2$–C$_4$ alkenyl group, the substituent for said lower alkyl or lower alkenyl group is selected from the group consisting of a halogen atom, a hydroxyl group, a carbamoyl group, an amino group and a cyano group, the substituent for said amino group is selected from the group consisting of a straight or branched C$_1$–C$_4$ alkyl group, a straight or branched C$_1$–C$_4$ alkycarbonyl group, a straight or branched C$_2$–C$_4$ alkenyl group and a benzylidene group which may have a phenyl group, and said halogen atom is selected from the group consisting of fluorine, chlorine, bromine and iodine atoms.

2. The compound according to claim 1, wherein R$_1$ to R$_4$ in the formula (2) are the same or different from one another and each represents a hydrogen atom, a halogen atom or a substituted or unsubstituted lower alkyl group, or two groups of R$_1$ and R$_2$ are optionally linked together to form a benzene ring; R$_5$ and m is an integer of 2 or 3.

3. A method for treating functional disorders of digestive organs, which comprises the step of administering to a subject in need of treatment a pharmaceutically effective amount of a serotonin 5-HT$_3$ receptor partial activator pharmaceutical composition comprising a compound represented by formula (2):

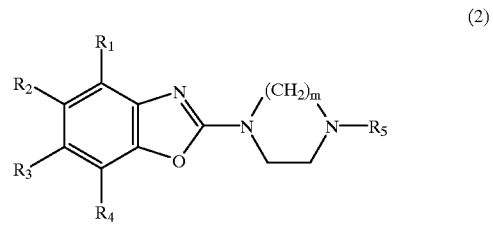

wherein R$_1$ to R$_4$ may be the same or different from one another and each represents a hydrogen atom, a halogen atom, a substituted or unsubstituted lower alkyl group, a substituted or unsubstituted lower alkenyl group or a substituted or unsubstituted amino group, or two groups of R$_1$ and R$_2$ may be linked together to form a benzene ring structure, with the proviso that compounds in-which all of R$_1$ to R$_4$ are hydrogen atoms are excluded; R$_5$ represents a hydrogen atom, a substituted or unsubstituted lower alkyl group or a substituted or unsubstituted lower alkenyl group; and m is an integer of 1 to 4, in which said lower alkyl group means a straight or branched C$_1$–C$_4$ alkyl group, said lower alkenyl group means a straight or branched C$_2$–C$_4$ alkenyl group, the substituent for said lower alkyl or lower alkenyl group is selected from the group consisting of a halogen atom, a hydroxyl group, a carbamoyl group, an amino group and a cyano group, the substituent for said amino group is selected from the group consisting of a straight or branched C$_1$–C$_4$ alkyl group, a straight or branched C$_1$–C$_4$ alkylcarbonyl group, a straight or branched C$_2$–C$_4$ alkenyl group and a benzylidene group which may have a phenyl group, and said halogen atom is selected from the group consisting of fluorine, chlorine, bromine and iodine atoms.

4. A method for treating diarrhea, which comprises the step of administering to a subject in need of treatment a pharmaceutically effective amount of a serotonin 5-HT$_3$ receptor partial activator pharmaceutical composition comprising a compound represented by formula (2):

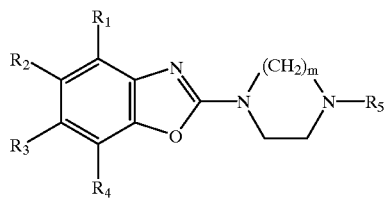

(2)

wherein $R_1$ to $R_4$ may be the same or different from one another and each represents a hydrogen atom, a halogen atom, a substituted or unsubstituted lower alkyl group, a substituted or unsubstituted lower alkenyl group or a substituted or unsubstituted amino group, or two groups of $R_1$ and $R_2$ may be linked together to form a benzene ring structure, with the proviso that compounds in-which all of $R_1$ to $R_4$ are hydrogen atoms are excluded; $R_5$ represents a hydrogen atom, a substituted or unsubstituted lower alkyl group or a substituted or unsubstituted lower alkenyl group; and m is an integer of 1 to 4, in which said lower alkyl group means a straight or branched $C_1$–$C_4$ alkyl group, said lower alkenyl group means a straight or branched $C_2$–$C_4$ alkenyl group, the substituent for said lower alkyl or lower alkenyl group is selected from the group consisting of a halogen atom, a hydroxyl group, a carbamoyl group, an amino group and a cyano group, the substituent for said amino group is selected from the group consisting of a straight or branched $C_1$–$C_4$ alkyl group, a straight or branched $C_1$–$C_4$ alkylcarbonyl group, a straight or branched $C_2$–$C_4$ alkenyl group and a benzylidene group which may have a phenyl group, and said halogen atom is selected from the group consisting of fluorine, chlorine, bromine and iodine atoms.

* * * * *